(12) United States Patent
MacDonald et al.

(10) Patent No.: US 7,727,513 B2
(45) Date of Patent: *Jun. 1, 2010

(54) METHOD FOR SCREENING FOR BACTERIAL CONJUNCTIVITIS

(75) Inventors: John Gavin MacDonald, Decatur, GA (US); Stephanie M. Martin, Woodstock, GA (US); Jason Lye, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 405 days.

This patent is subject to a terminal disclaimer.

(21) Appl. No.: 11/303,001

(22) Filed: Dec. 15, 2005

(65) Prior Publication Data

US 2007/0140971 A1 Jun. 21, 2007

(51) Int. Cl.
*A61K 49/00* (2006.01)
*C12Q 1/20* (2006.01)
*C12Q 1/22* (2006.01)
*C12Q 1/04* (2006.01)

(52) U.S. Cl. .................... 424/9.6; 435/29; 435/31; 435/34

(58) Field of Classification Search .............. None
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,763 A | 3/1970 | Hartmann |
| 3,542,615 A | 11/1970 | Dobo et al. |
| 3,692,618 A | 9/1972 | Dorschner et al. |
| 3,705,032 A | 12/1972 | Honjo et al. |
| 3,802,817 A | 4/1974 | Matsuki et al. |
| 3,849,241 A | 11/1974 | Butin et al. |
| 4,100,324 A | 7/1978 | Anderson et al. |
| 4,310,928 A | 1/1982 | Joung |
| 4,340,395 A | 7/1982 | Magers et al. |
| 4,340,563 A | 7/1982 | Appel et al. |
| 4,375,448 A | 3/1983 | Appel et al. |
| 4,494,278 A | 1/1985 | Kroyer et al. |
| 4,511,488 A | 4/1985 | Matta |
| 4,556,636 A | 12/1985 | Belly et al. |
| 4,640,810 A | 2/1987 | Laursen et al. |
| 4,677,076 A | 6/1987 | Langhals |
| 4,775,582 A | 10/1988 | Abba et al. |
| 4,780,422 A | 10/1988 | Mitani et al. |
| 4,818,464 A | 4/1989 | Lau |
| 4,833,003 A | 5/1989 | Win et al. |
| 4,853,281 A | 8/1989 | Win et al. |
| 5,036,000 A | 7/1991 | Palmer et al. |
| 5,112,900 A | 5/1992 | Buddenhagen et al. |
| 5,407,715 A | 4/1995 | Buddenhagen et al. |
| 5,464,739 A | 11/1995 | Johnson et al. |
| 5,468,469 A | 11/1995 | Aszalos et al. |
| 5,527,171 A | 6/1996 | Soerensen |
| 5,534,416 A * | 7/1996 | Millard et al. ............... 436/34 |
| 5,742,943 A | 4/1998 | Chen |
| 5,744,321 A | 4/1998 | Harewood |
| 5,792,531 A | 8/1998 | Littleton et al. |
| 5,900,452 A | 5/1999 | Plamthottam |
| 6,090,541 A | 7/2000 | Wicks et al. |
| 6,306,514 B1 | 10/2001 | Weikel et al. |
| 6,362,006 B1 | 3/2002 | Potyrailo et al. |
| 6,368,558 B1 * | 4/2002 | Suslick et al. ............... 422/55 |
| 6,383,815 B1 | 5/2002 | Potyrailo |
| 6,524,846 B1 | 2/2003 | Robinson, Jr. |
| 2003/0119202 A1 | 6/2003 | Kaylor et al. |
| 2003/0143112 A1* | 7/2003 | Suslick et al. ............... 422/55 |
| 2005/0130253 A1* | 6/2005 | Lye et al. .................... 435/29 |

(Continued)

FOREIGN PATENT DOCUMENTS

EP 0266196 A2 5/1988

(Continued)

OTHER PUBLICATIONS

Knauf HP et al (1996) Susceptibility of corneal and conjunctival pathogens to ciprofloxacin. Cornea, vol. 15, No. 1, pp. 66-71.*

(Continued)

*Primary Examiner*—Lisa J Hobbs
*Assistant Examiner*—Jon P Weber
(74) *Attorney, Agent, or Firm*—Dority & Manning, P.A.

(57) ABSTRACT

A method for rapidly detecting infectious conjunctivitis in a host is provided. The method includes contacting an ocular test sample with a chromogen (e.g., Reichardt's dye) that exhibits a color change in the presence of a microbe. The present inventors have discovered that the extent of the color change may vary depending on whether the microbe is a bacteria or virus. Without intending to be limited by theory, the present inventors believe that the chromogen interacts with the peptidoglycan-based cell wall structure of bacteria to induce a color change that is even more apparent at infectious levels. It is believed that this interaction occurs to a much greater extent in bacteria than in viruses. Accordingly, although the chromogen may still undergo a color change in the presence of the viruses, it is typically to a much lesser extent. In this manner, the degree of color change of the chromogen may be used in the present invention as a mechanism for differentiating between viral and bacterial conjunctivitis.

14 Claims, 5 Drawing Sheets

U.S. PATENT DOCUMENTS

| | | | |
|---|---|---|---|
| 2006/0134613 | A1 | 6/2006 | Martin et al. |
| 2006/0134728 | A1* | 6/2006 | MacDonald et al. .......... 435/34 |

FOREIGN PATENT DOCUMENTS

| | | |
|---|---|---|
| EP | 0266196 A3 | 5/1988 |
| EP | 0846767 A | 6/1998 |
| GB | 1107790 | 3/1968 |
| GB | 2178847 A | 2/1987 |
| WO | WO 9730351 A1 | 8/1997 |
| WO | WO 0233413 A1 | 4/2002 |
| WO | WO 02103356 A1 | 12/2002 |
| WO | WO 2005016230 A | 2/2005 |

OTHER PUBLICATIONS

Vidal-Mas J et al (2001) Rapid flow cytometry—Nile red assessment of PHA cellular content and heterogeneity in cultures of *Pseudomonas aeruginosa* 47T2 (NCIB 40044) grown in waste frying oil. Antonie van Leeuwenhoek, vol. 80, pp. 57-63.*

Davey HM et al (Dec. 1996) Flow cytometry and cell sorting of heterogeneous microbial populations: the importance of single-cell analyses. Microbiol Rev, vol. 60, No. 4, pp. 641-696.*

Reichardt C (1994) Solvatochromic dyes as solvent polarity indicators. Chem Rev, vol. 94, pp. 2319-2358.*

Abstract of Japanese Patent No. JP11083849 with XP-002327939 Mar. 26, 1999.

Abstract of Article—$A^TH$ NMR Investigation Concerning the Insertion of Pyridinium N-Phenoxide Betaines into Micelles, Plieninger et al., Liebigs Ann. Chem. 1983, pp. 860-875.

Article—*Colour and Constitution of Organic Molecules*, John Griffiths, Academic Press, 1976, pp. 16-80 and pp. 146-160.

Article—*Solvent dependent hyperpolarizability of a merocyanine dye*, Levine et al., J. Chem. Phys., vol. 68, No. 11, Jun. 1, 1978, pp. 5042-5045.

Article—*Investigation of Micelles, Microemulsions, and Phospholipid Bilayers with the Pyridinium N-Phenolbetaine Er(30), a Polarity Probe for Aqueous Interfaces*, Zachariasse et al., J. Phys. Chem., vol. 85, No. 18, Sep. 3, 1981, pp. 2676-2683.

Article—*Synthesis and structure-property relationships of amphiphilic acidochromic hydroxystilbazolium dyes*, Lehmann et al., Sensors and Actuators B 38-39, 1997, pp. 229-234.

Article—*Second order hyperpolarizability of hydroxystilbazolium salts and their betaines—relationship to chemical structure*, Grummt et al., J. Mater. Chem., vol. 9, 1999, pp. 1419-1424.

Article—*Nile Red: A Selective Fluorescent Stain for Intracellular Lipid Droplets*, Greenspan et al., The Journal of Cell Biology, vol. 100, Mar. 1985, pp. 965-973.

Article—*Pyridinium N-phenolate betaine dyes as empirical indicators of solvent polarity: Some new findings*, Reichardt, Pure Appl. Chem., vol. 76, No. 10, 2004, pp. 1903-1919.

Pocket Guide to Digital Printing, Frank Cost, Delmar Publishers, Albany, NY, ISBN 0-8273-7592-1, pp. 144-145, 1996.

Article—*Potential Antitumor Phenoxazines*, Motohashi et al., Medicinal Research Reviews, vol. 11, No. 3, May 1991, pp. 239-294.

Article—*The Change in Research for the Therapy of Tumors*, Sedlacek et al., Chimia, vol. 45, No. 10, Oct. 1991, pp. 311-316.

Chapters 6 and 9-11 from book entitled *Photodynamic Action and Diseases Caused by Light* by Harold Francis Blum, American Chemical Society Series of Scientific and Technologic Monographs, 1941.

Article—Rapid Diagnosis of Adenoviral Keratoconjunctivitis by a Fully Automated Molecular Assay, Koidl et al., Ophthalmology, vol. 112, No. 9, Sep. 2005, pp. 1521.e1-1521.e8.

Article—Simplifying Collection of Corneal Specimens in Cases of Suspected Bacterial Keratitis, Kaye et al., Journal of Clinical Microbiology, vol. 41, No. 7, Jul. 2003, pp. 3192-3197.

Article—Development and Use of Nested Polymerase Chain Reaction (PCR) for the Detection of Adenovirus from Conjunctivitis Specimens, Dalapathy, et al., Journal of Clinical Virology 11, 1998, pp. 77-84.

Article—Chloramphenicol Treatment for Acute Infective Conjunctivitis in Children in Primary Care: A Randomised Double-Blind Placebo-Controlled Trial, Rose et al., The Lancet, vol. 366, Jul. 2, 2005, pp. 37-43.

Standard Practice for Obtaining Spectrometric Data for Object-Color Evaluation, ASTM International, E-1164, 2002, pp. 1-8.

Paints and Varnishes—Colorimetry—Part 1: Principles, International Standard ISO 7724/1-1984 (E), Oct. 1, 1984.

Methods of Colour Measurement—Reflecting and Transmitting Objects, Japanese Industrial Standard, JIS Z 8722:2000 (E).

Colorimetry, 2nd Edition, International Commission on Illumination, No. 15.2, 1986.

Article—Ocular Virulence of Capsule-Deficient *Streptococcus pneumoniae* in a Rabbit Keratitis Model, Reed et al., Investigative Ophthalmology & Visual Science, Feb. 2005, vol. 46, No. 2, pp. 604-608.

Abstract of Detection of Adenovirus DNA in Clinical Samples by SYBR Green Real-Time Polymerase Chain Reaction Assay, Watanabe et al., (2005) Pedatr. Int. 47(3): 286-91.

Abstract of Antimicrobial Resistance Among Clinical Isolates of *Haemophilus influenzae* in Northern Italy. Vollaborative Study on Pediatric Infectious Diseases, Garlaschi, et al., (1993) Eur. J. Epidimiol. 9(1): 64-9.

* cited by examiner

METHOD FOR SCREENING FOR BACTERIAL CONJUNCTIVITIS

BACKGROUND OF THE INVENTION

Conjunctivitis is the most common eye disorder and may vary in severity from a mild inflammation with tearing to a severe inflammation that causes tissue injury. Infectious conjunctivitis is generally caused by the presence of bacteria or viruses. A variety of bacteria may cause bacterial conjunctivitis, such as *S. pneumoniae, H. influenzae, P. aeruginosa*, or *S. pyogenes*. Likewise, a variety of viruses may be responsible for viral conjunctivitis, such as adenovirus, herpes simplex virus (HSV), varicella-zoster virus (VZV), picornavirus (enterovirus 70, Coxsackie A24), poxvirus (molluscum contagiosum, vaccinia), and human immunodeficiency virus (HIV). Adenoviral conjunctivitis is the most common cause of viral conjunctivitis. Particular subtypes of adenoviral conjunctivitis include epidemic keratoconjunctivitis (pink eye) and pharyngoconjunctival fever. Primary ocular herpes simplex infection is also common, particularly in children, and is normally associated with a follicular conjunctivitis.

The treatment protocol for infectious conjunctivitis largely depends on whether the infection is viral or bacterial. Viral conjunctivitis is self-limiting and may require no specific treatment, other than drops to alleviate any symptoms associated with the infection. On the other hand, patients having bacterial conjunctivitis are typically treated with topical antibiotics (e.g., sulfacetamide sodium 10% drops or trimethoprim/polymyxin B qid). Conventional techniques for diagnosing the type of ocular infection rely primarily on clinical examination. For example, because the discharge in bacterial conjunctivitis is usually more purulent than the watery discharge of viral conjunctivitis, physical examination may be used in the diagnosis. Unfortunately, such diagnostic techniques are often unreliable and lead to the prescription of antibiotic drops in cases in which they are not needed.

As such, a need currently exists for a technique of rapidly screening for bacterial conjunctivitis in a patient.

SUMMARY OF THE INVENTION

In accordance with one embodiment of the present invention, a method for screening for bacterial conjunctivitis is disclosed. The method comprises contacting an ocular test sample with a chromogen. The chromogen undergoes a detectable color change in less than about 30 minutes in the presence of bacteria at a pathogenic concentration.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "ocular test sample" generally refers to a biological material obtained directly or indirectly from the eye of a host, such as from ocular lens fluid (e.g., tears), discharge, tissue, etc. The test sample may be obtained in by any method desired, such as using a swab. The test sample may also be used as obtained or pretreated in some manner. For example, such pretreatment may include filtration, precipitation, dilution, distillation, mixing, concentration, inactivation of interfering components, the addition of reagents, lysing, etc.

As used herein, the term "host" refers to any animal, preferably a human.

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a method for rapidly screening for bacterial conjunctivitis in a host. The method includes contacting an ocular test sample with a chromogen (e.g., Reichardt's dye) that exhibits a color change in the presence of a microbe. The present inventors have discovered that the extent of the color change may vary depending on whether the microbe is a bacteria or virus. Without intending to be limited by theory, the present inventors believe that the chromogen interacts with the peptidoglycan-based cell wall structure of bacteria to induce a color change that is even more apparent at infectious levels. It is believed that this interaction occurs to a much greater extent in bacteria than in viruses. Accordingly, although the chromogen may still undergo a color change in the presence of the viruses, it is typically to a much lesser extent. In this manner, the degree of color change of the chromogen may be used in the present invention as a mechanism for differentiating between viral and bacterial conjunctivitis.

Any of a variety of bacteria and/or viruses may be detected in accordance with the present invention. For example, gram-positive cocci (e.g., *Staphylococcus epidermidis, Streptococcus pyogenes*, and *Streptococcus pneumoniae*); gram-negative cocci (e.g., *P. aeruginosa, Neisseria meningitides*, and *Moraxella lacunata*); and gram-negative rods (e.g., *Haemophilus influenzae*) are often associated with bacterial conjunctivitis and may be detected in the present invention. Gram-negative bacteria have a cell wall coated with lipopolysaccharide (LPS). Gram-positive bacteria are coated with thick peptidoglycan (or murein) sheet-like layers. The most prevalent causes of bacterial conjunctivitis are *Streptococcus pneumoniae, Haemophilus influenzae*, or *Streptococcus pyogenes. Streptococcus pyogenes* is a Gram-positive, nonmotile, nonsporeforming cocci that occurs in chains or in pairs of cells. *Streptococcus pyogenes* is a catalase-negative aerotolerant anaerobe (facultative anaerobe) and requires enriched medium containing blood in order to grow. *Haemophilus influenzae* is a small, nonmotile Gram-negative bacterium in the family Pasteurellaceae. Non-encapsulated strains of *Haemophilus influenzae* are believed to primarily cause conjunctivitis.

Viruses contain a nucleic acid enclosed within a protein organized in capsomer subunits ("capsid"). Some viruses also contain a glycoprotein envelope surrounding the capsid that is composed of two lipid layers interspersed with protein molecules (lipoprotein bilayer) and may contain material from the membrane of a host cell or viral origin. Viruses may also develop spikes made of glycoprotein on their envelopes that help them to attach to specific cell surfaces. The most common form of viral conjunctivitis that may be detected in accordance with the present invention is caused by adenoviruses of the family Adenoviridae. Epidemic keratoconjunctivitis, for example, is associated with adenovirus serotypes 8, 19, and 37. Adenoviruses are double-stranded DNA viruses that contain icosahedral capsids with twelve vertices and seven surface proteins. The virion is non-enveloped and spherical. Herpes viruses are also commonly associated with viral conjunctivitis. Herpes viruses contain icosahedral capsids surrounded by a thick layer of additional proteins (Tegument) and an outer envelope with spike-like glycoproteins. The capsid contains 162 capsomers enclosing a core structure containing double-stranded linear viral DNA. Herpes viruses are classified into three groups based on tissue tropism, pathogenicity, and behavior under culture conditions in the laboratory, i.e., α-, β- and γ-herpes viruses. Herpes simplex virus type 1 and 2 (HSV-1 and HSV-2) are in the α-subfamily of herpes viruses. HSV-1 is most commonly associated with viral conjunctivitis.

The chromogen is selected in accordance with the present invention to interact in some manner with the cell membrane of the microbe and/or the environment in which the microbe is present. As a result of this interaction, the chromogen undergoes a change in color that is readily detectable (e.g., with an unaided eye). The term "color" relates to the presence or absence of certain wavelengths of light reflected or emitted from objects in a visual field. Light entering the eye, for example, is subjected to a spectral analysis by three types of retinal cone cells that are sensitive to specific regions of the visible spectrum. Stimuli from these cells are in turn processed by retinal neurons, optic nerve neurons and the visual cortex so that a sensation of color is experienced. The chromogen employed in the present invention typically owes its color to the absorption of certain wavelengths of light. As such, the perceived color is usually the complement of the color associated with the wavelength of light being absorbed by the object. An object that appears to be red in color when viewed in white light, for example, is in fact selectively absorbing bluish light in the wavelength range of 490 to 500 nanometers. Similarly, an object that appears yellow in white light is in fact absorbing blue light in the wavelength range of 435 to 480 nanometers.

The absorption of visible light is associated with electronic transitions within a molecule and results in the generation of an excited state. The energy difference between the ground state of the molecule and the relevant excited state determines the wavelength of the light absorbed according to the Planck relationship:

$$E = h\nu$$

wherein,

E is energy, h is Planck's constant, and $\nu$ is the frequency of the photon of light absorbed, and is related to wavelength $\lambda$ and the speed of light c by $\nu = c/\lambda$.

A state diagram, such as shown below, may be used to graphically depict electronic transitions:

The energy of an absorbed photon is thus inversely proportional to the wavelength of the photon. Thus, photons of blue light (435-480 nanometers) have a higher energy than yellow light (580-595 nanometers). As such, the color of the chromogen is determined by the transition energy between the ground state of the chromogen and the first allowed excited state.

The light-absorbing portion of the chromogen employed in the present invention is a chromophore that is generally responsible for the color of the chromogen and is connected to a conjugated system. For instance, azo groups (e.g., azo dyes), polyene groups (e.g., carotene dye), carbonyl groups (e.g., anthraquinone dyes) are common chromophores. Auxochromes may induce a shift of the absorption maxima of the chromophore towards either the red end of the spectrum ("bathochromic shift") or the blue end of the spectrum ("hypsochromic shift"). Auxochromes may or may not be conjugated with the chromogen. For instance, an amino group conjugated to an azo group (chromophore) via, for instance, a benzene ring, will form an aminoazo chromogen. The type of absorption shift depends on the nature of the chromophore and, for example, on whether the auxochrome functions as an electron acceptor, in which a hypsochromic shift results, or whether the amino group functions as an electron donor, in which a bathochromic shift results. For example, a conjugated amino auxochrome will shift the absorption band of the azo group to longer wavelengths and increases the intensity of the absorption band. The absorption shift provides a color difference that is detectable, either visually or through instrumentation.

One particularly suitable class of chromogens that may undergo a detectable color change in the presence of bacteria is solvatochromic dyes. Solvatochromic dyes are dyes having spectroscopic characteristics (e.g., absorption) in the ultra-violet/visible/near-infrared spectrum and are sometimes influenced by the surrounding medium. The solvatochromic dyes may be positive or negative, which corresponds to bathochromic and hypsochromic shifts, respectively, of the emission band with increasing solvent polarity. In one embodiment, for instance, the solvatochromic dye undergoes a color change in a certain molecular environment based on solvent polarity and/or hydrogen bonding propensity. For example, a solvatochromic dye may be blue in a polar environment (e.g., water), but yellow or red in a non-polar environment (e.g., lipid-rich solution). The color produced by the solvatochromic dye depends on the molecular polarity difference between the ground and excited state of the dye.

Merocyanine dyes (e.g., mono-, di-, and tri-merocyanines) are one example of a type of solvatochromic dye that may be employed in the present invention. Merocyanine dyes, such as merocyanine 540, fall within the donor-simple acceptor chromogen classification of Griffiths as discussed in "Colour and Constitution of Organic Molecules" Academic Press, London (1976). More specifically, merocyanine dyes have a basic nucleus and acidic nucleus separated by a conjugated chain having an even number of methine carbons. Such dyes possess a carbonyl group that acts as an electron acceptor moiety. The electron acceptor is conjugated to an electron donating group, such as a hydroxyl or amino group. The merocyanine dyes may be cyclic or acyclic (e.g., vinylalogous amides of cyclic merocyanine dyes). For example, cyclic merocyanine dyes generally have the following structure:

wherein, n is any integer, including 0. As indicated above by the general structures 1 and 1', merocyanine dyes typically have a charge separated (i.e., "zwifterionic") resonance form. Zwitterionic dyes are those that contain both positive and negative charges and are net neutral, but highly charged. Without intending to be limited by theory, it is believed that the zwitterionic form contributes significantly to the ground state of the dye. The color produced by such dyes thus depends on the molecular polarity difference between the ground and excited state of the dye. One particular example of a merocyanine dye that has a ground state more polar than the excited state is set forth below as structure 2.

The charge-separated left hand canonical 2 is a major contributor to the ground state whereas the right hand canonical 2' is a major contributor to the first excited state. Still other examples of suitable merocyanine dyes are set forth below in the following structures 3-13.

3

-continued

4

5

6

7

-continued

8

-continued

9

10

11

12

13 wherein, "R" is a group, such as methyl, alkyl, aryl, phenyl, etc.

Indigo is another example of a suitable solvatochromic dye for use in the present invention. Indigo has a ground state that is significantly less polar than the excited state. For example, indigo generally has the following structure 14:

The left hand canonical form 14 is a major contributor to the ground state of the dye, whereas the right hand canonical 14' is a major contributor to the excited state.

Other suitable solvatochromic dyes that may be used in the present invention include those that possess a permanent zwitterionic form. That is, these dyes have formal positive and negative charges contained within a contiguous π-electron system. Contrary to the merocyanine dyes referenced above, a neutral resonance structure cannot be drawn for such permanent zwitterionic chromogens. Exemplary dyes of this class include N-phenolate betaine dyes, such as those having the following general structure:

wherein $R_1$-$R_5$ are independently selected from the group consisting of hydrogen, a nitro group (e.g., nitrogen), a halogen, or a linear, branched, or cyclic $C_1$ to $C_{20}$ group (e.g., alkyl, phenyl, aryl, pyridinyl, etc.), which may be saturated or unsaturated and unsubstituted or optionally substituted at the same or at different carbon atoms with one, two or more halogen, nitro, cyano, hydroxy, alkoxy, amino, phenyl, aryl, pyridinyl, or alkylamino groups. For example, the N-phenolate betaine dye may be 4-(2,4,6-triphenylpyridinium-1-yl)-2,6-diphenylphenolate (Reichardt's dye) having the following general structure 15:

15

Reichardt's dye shows strong negative solvatochromism. That is, Reichardt's dye displays a shift in absorbance to a shorter wavelength and thus has visible color changes as solvent eluent strength (polarity) increases. Still other examples of suitable negatively solvatochromic pyridinium N-phenolate betaine dyes are set forth below in structures 16-23:

16 wherein, R is hydrogen, —C(CH$_3$)$_3$, —CF$_3$, or C$_6$F$_{13}$.

17

18

-continued

19

20

21

22

-continued

23

Still additional examples of dyes having a permanent zwitterionic form include dyes having the following general structure 24:

24 wherein, n is 0 or greater, and X is oxygen, carbon, nitrogen, sulfur, etc. Particular examples of the permanent zwitterionic dye shown in structure 24 include the following structures 25-33.

-continued

Still other suitable solvatochromic dyes may include, but are not limited to 4-dicyanmethylene -2-methyl-6-(p-dimethylaminostyryl)-4H-pyran (DCM); 6-propionyl -2-(dimethylamino)naphthalene (PRODAN); 9-(diethylamino)-5H-benzo[a]phenox-azin-5-one (Nile Red); 4-(dicyanovinyl) julolidine (DCVJ); phenol blue; stilbazolium dyes; coumarin dyes; ketocyanine dyes; N,N-dimethyl-4-nitroaniline (ND-MNA) and N-methyl-2-nitroaniline (NM2NA); Nile blue; 1-anilinonaphthalene -8-sulfonic acid (1,8-ANS), and dapoxylbutylsulfonamide (DBS) and other dapoxyl analogs. Besides the above-mentioned dyes, still other suitable dyes that may be used in the present invention include, but are not limited to, 4-[2-N-substituted -1,4-hydropyridin-4-ylidine) ethylidene]cyclohexa-2,5-dien-1-one, red pyrazolone dyes, azomethine dyes, indoaniline dyes, and mixtures thereof.

Although the above-referenced dyes are classified as solvatochromic, it should be understood that the present invention is not necessarily limited to any particular mechanism for the color change of the chromogen. Even when a solvatochromic dye is employed, other mechanisms may actually be wholly or partially responsible for the color change of the dye. For example, acid-base or proton donation reactions between the dye and microbe may result in the color change. As an example, highly organized acid moieties on bacteria cell walls may protonate certain dyes, resulting in a loss of color. Redox reactions between the dye and microbe may likewise contribute to the color change.

The chromogen may be used alone or as part of a detection composition. If desired, the detection composition may contain a carrier for the chromogen that functions as a mobile phase. The carrier may be a liquid, gas, gel, etc., and may be selected to provide the desired performance (time for change of color, contrast between different areas, and sensitivity) of the chromogen. In some embodiments, for instance, the carrier may be an aqueous solvent, such as water, as well as a non-aqueous solvent, such as glycols (e.g., propylene glycol, butylene glycol, triethylene glycol, hexylene glycol, polyethylene glycols, ethoxydiglycol, and dipropyleneglycol); alcohols (e.g., methanol, ethanol, n-propanol, and isopropanol); triglycerides; ethyl acetate; acetone; triacetin; acetonitrile; tetrahydrafuran; xylenes; formaldehydes (e.g., dimethylformamide); etc. The amount of the carrier and chromogen in the detection composition may generally vary based on the level of microbe sensitivity and-color pattern or design utilized. For instance, in some embodiments, the chromogen may be present in the detection composition at a concentration from about 0.1 to about 100 milligrams per milliliter of carrier, in some embodiments from about 0.5 to about 60 milligrams per milliliter of carrier, and in some embodiments, from about 1 to about 40 milligrams per milliliter of carrier.

Besides the chromogen and carrier, the detection composition may also contain a variety of other components. In one embodiment, for instance, additives are incorporated into the detection composition that enhance the performance of the chromogen. For example, cyclodextrins may enhance the sensitivity of the chromogen and the contrast between regions that regions of different color. While not wishing to be bound by theory, the present inventors believe that such additives may inhibit the crystallization of the dye and thus provide a more vivid color and also enhance detection sensitivity. That is, single dye molecules have greater sensitivity for microbes because each dye molecule is free to interact with the microbial membrane. In contrast, small crystals of dye have to first dissolve and then penetrate the membrane. Examples of suitable cyclodextrins may include, but are not limited to, hydroxypropyl-β-cyclodextrin, hydroxyethyl-β-cyclodextrin, γ-cyclodextrin, hydroxypropyl-γ-cyclodextrin, and hydroxyethyl-γ-cyclodextrin, which are commercially available from Cerestar International of Hammond, Ind.

Surfactants may also help enhance the sensitivity of the chromogen and the contrast between different regions. Particularly desired surfactants are nonionic surfactants, such as ethoxylated alkylphenols, ethoxylated and propoxylated fatty alcohols, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, acetylenic diols, and mixtures thereof. Various specific examples of suitable nonionic surfactants include, but are not limited to, methyl gluceth-10, PEG-20 methyl glucose distearate, PEG-20 methyl glucose sesquistearate, $C_{11-15}$ pareth -20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene -20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene -6 tridecyl ether, laureth-2, laureth-3, laureth-4, PEG-3 castor oil, PEG 600 dioleate, PEG 400 dioleate, and mixtures thereof. Commercially available nonionic surfactants may include the SURFYNOL® range of acetylenic diol surfactants available from Air Products and Chemicals of Allentown, Pa. and the TWEEN® range of polyoxyethylene surfactants available from Fischer Scientific of Pittsburgh, Pa.

The detection composition may also contain a binder to facilitate the immobilization of the chromogen on a substrate. For example, water-soluble organic polymers may be employed as binders. One suitable class of water-soluble organic polymers includes polysaccharides and derivatives thereof. Polysaccharides are polymers containing repeated carbohydrate units, which may be cationic, anionic, nonionic, and/or amphoteric. In one particular embodiment, the polysaccharide is a nonionic, cationic, anionic, and/or amphoteric cellulosic ether. Suitable nonionic cellulosic ethers may include, but are not limited to, alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, methyl hydroxypropyl cellulose, ethyl hydroxyethyl cellulose, ethyl hydroxypropyl cellulose, methyl ethyl hydroxyethyl cellulose and methyl ethyl hydroxypropyl cellulose; and so forth.

If desired, the detection composition may be applied to a substrate, which is subsequently contacted with the infected test sample. Suitable application techniques include printing, dipping, spraying, melt extruding, coating (e.g., solvent coating, powder coating, brush coating, etc.), and so forth. Upon application, the detection composition is dried to remove the carrier and leave a residue of the chromogen for interacting with a microbe. For example, the detection composition may be printed onto a surface of the substrate to signal the presence of microbes upon a change in color. The detection composition may cover all or only a portion of the substrate surface. In one embodiment, for example, the detection composition is printed in the form of indicia that conveys a certain message to the user. The substrate may be formed from any of a variety materials capable of being applied with the detection composition. For example, the substrate may be formed from film, paper, a nonwoven fabric, a knitted fabric, a woven fabric, foam, etc. The substrate may be incorporated into a wide variety of articles, such as strips, lateral flow devices, stickers, test kits, swab & know cards, facial tissues, diapers, throat swabs, wound dressings, and so forth. In one particular embodiment, the substrate is a facestock material commonly employed in the manufacture of labels, such as paper, polyester, polyethylene, polypropylene, polybutylene, polyamides, etc. An adhesive, such as a pressure-sensitive adhesive, heat-activated adhesive, hot melt adhesive, etc., may be employed on one or more surfaces of the facestock material to help adhere it to a surface. Suitable examples of pressure-sensitive adhesives include, for instance, acrylic-based adhesives and elastomeric adhesives. In one embodiment, the pressure-sensitive adhesive is based on copolymers of acrylic acid esters (e.g., 2-ethyl hexyl acrylate) with polar co-monomers (e.g., acrylic acid). The adhesive may have a thickness in the range of from about 0.1 to about 2 mils (2.5 to 50 microns). A release liner may also be employed that contacts the adhesive prior to use. The release liner may contain any of a variety of materials known to those of skill in the art, such as a silicone-coated paper or film substrate. Although the discussion above refers to the application of the detection composition to the substrate, it should be understood that additive(s) may also be applied separately from the chromogen-containing detection composition.

Regardless of the manner in which it is applied, the amount of the chromogen employed is effective to result in a detectable color change upon contact with bacteria. The exact quantity may vary based on a variety of factors, including the sensitivity of the chromogen, the presence of other additives in the detection composition, the desired degree of detectability (e.g., with an unaided eye), the suspected concentration of the microbe, etc. In some cases, it is desirable to only detect the presence of bacteria at concentrations that are considered pathogenic. For example, a bacteria concentration of about $1\times10^5$, in some embodiments about $1\times10^6$, and in some embodiments, about $1\times10^8$ colony forming units ("CFU") per milliliter of a test sample may be considered a threshold pathogenic concentration for bacterial conjunctivitis. Thus, the chromogen may be present in an amount sufficient to undergo a detectable color change in the presence of bacteria at a concentration of at least about $1 \times 10^8$ CFU per milliliter of the test sample. For example, when present on a substrate, the chromogen may constitute from about 0.001 wt. % to about 20 wt. %, in some embodiments from about 0.01 wt. % to about 10 wt. %, and in some embodiments from about 0.1 wt. % to about 5 wt. % of the dry weight of the substrate. The amount of other additives (e.g., cyclodextrins, surfactants, binders, etc.) may also vary as desired, such as from about 0.001 wt. % to about 10 wt. %, in some embodiments from about 0.01 wt. % to about 5 wt. %, and in some embodiments from about 0.025 wt. % to about 1 wt. % based on the dry weight of the substrate.

As stated above, the degree to which the chromogen changes color provides information regarding the presence of bacteria or virus to which it is exposed. For example, Reichardt's dye shows strong negative solvatochromism and may thus undergo a significant color change from blue to colorless in the presence of bacteria. In the presence of certain viruses, the color change occurs to a lesser extent if at all. Thus, when an infected test sample is placed into contact with the dye, the color change may simply be observed to determine whether the infection is caused by bacteria. That is, if the color change occurs to a certain degree (e.g., from blue to colorless), it may be determined that the infected test sample contains bacteria. Likewise, if a color change occurs to a lesser extent (e.g., from blue to faint blue), it may be determined that the test sample contains an infectious level of a virus or that the conjunctivitis is simply due to non-infectious causes, such as allergenic conjunctivitis. In either case, however, it will become readily apparent whether or not an antibiotic is needed.

The color of a reacted test chromogen may be compared (e.g., visually or with the aid of an instrument) to the color of a control chromogen, which is formed from a compound that is the same or similar to the test chromogen with respect to its responsiveness to microbes. Multiple control chromogens may likewise be employed that correspond to different types of bacteria at the threshold pathogenic concentration. Upon comparison, one or more of the control chromogens may be selected that have a color that is the same or substantially similar to a test chromogen reacted with a test sample. The type of microbe within the test sample is then determined from the selected control chromogen(s) and the corresponding known microbe(s).

The degree to which the chromogen changes color may be determined either visually or using instrumentation. In one embodiment, color intensity is measured with an optical reader. The actual configuration and structure of the optical reader may generally vary as is readily understood by those skilled in the art. Typically, the optical reader contains an illumination source that is capable of emitting electromagnetic radiation and a detector that is capable of registering a signal (e.g., transmitted or reflected light). The illumination source may be any device known in the art that is capable of providing electromagnetic radiation, such as light in the visible or near-visible range (e.g., infrared or ultraviolet light). For example, suitable illumination sources that may be used in the present invention include, but are not limited to, light emitting diodes (LED), flashlamps, cold-cathode fluorescent lamps, electroluminescent lamps, and so forth. The illumination may be multiplexed and/or collimated. In some cases, the illumination may be pulsed to reduce any background interference. Further, illumination may be continuous or may combine continuous wave (CW) and pulsed illumination where multiple illumination beams are multiplexed (e.g., a pulsed beam is multiplexed with a CW beam), permitting signal discrimination between a signal induced by the CW source and a signal induced by the pulsed source. For example, in some embodiments, LEDs (e.g., aluminum gallium arsenide red diodes, gallium phosphide green diodes, gallium arsenide phosphide green diodes, or indium gallium nitride violet/blue/ultraviolet (UV) diodes) are used as the pulsed illumination source. One commercially available example of a suitable UV LED excitation diode suitable for use in the present invention is Model NSHU55 OE (Nichia Corporation), which emits 750 to 1000 microwatts of optical power at a forward current of 10 milliamps (3.5-3.9 volts) into a beam with a full-width at half maximum of 10 degrees, a peak wavelength of 370-375 nanometers, and a spectral half-width of 12 nanometers.

In some cases, the illumination source may provide diffuse illumination to the chromogen. For example, an array of multiple point light sources (e.g., LEDs) may simply be employed to provide relatively diffuse illumination. Another particularly desired illumination source that is capable of providing diffuse illumination in a relatively inexpensive manner is an electroluminescent (EL) device. An EL device is generally a capacitor structure that utilizes a luminescent material (e.g., phosphor particles) sandwiched between electrodes, at least one of which is transparent to allow light to escape. Application of a voltage across the electrodes generates a changing electric field within the luminescent material that causes it to emit light.

The detector may generally be any device known in the art that is capable of sensing a signal. For instance, the detector may be an electronic imaging detector that is configured for spatial discrimination. Some examples of such electronic imaging sensors include high speed, linear charge-coupled devices (CCD), charge-injection devices (CID), complementary-metal-oxide-semiconductor (CMOS) devices, and so forth. Such image detectors, for instance, are generally two-dimensional arrays of electronic light sensors, although linear imaging detectors (e.g., linear CCD detectors) that include a single line of detector pixels or light sensors, such as, for example, those used for scanning images, may also be used. Each array includes a set of known, unique positions that may be referred to as "addresses." Each address in an image detector is occupied by a sensor that covers an area (e.g., an area typically shaped as a box or a rectangle). This area is generally referred to as a "pixel" or pixel area. A detector pixel, for instance, may be a CCD, CID, or a CMOS sensor, or any other device or sensor that detects or measures light. The size of detector pixels may vary widely, and may in some cases have a diameter or length as low as 0.2 micrometers.

In other embodiments, the detector may be a light sensor that lacks spatial discrimination capabilities. For instance, examples of such light sensors may include photomultiplier devices, photodiodes, such as avalanche photodiodes or silicon photodiodes, and so forth. Silicon photodiodes are sometimes advantageous in that they are inexpensive, sensitive, capable of high-speed operation (short risetime/high bandwidth), and easily integrated into most other semiconductor technology and monolithic circuitry. In addition, silicon photodiodes are physically small, which enables them to be readily incorporated into various types of detection systems. If silicon photodiodes are used, then the wavelength range of the emitted signal may be within their range of sensitivity, which is 400 to 1100 nanometers.

Optical readers may generally employ any known detection technique, including, for instance, luminescence (e.g., fluorescence, phosphorescence, etc.), absorbance (e.g., fluorescent or non-fluorescent), diffraction, etc. In one particular embodiment of the present, the optical reader measures color intensity as a function of absorbance. In one embodiment, absorbance readings are measured using a microplate reader from Dynex Technologies of Chantilly, Virginia (Model # MRX). In another embodiment, absorbance readings are measured using a conventional test known as "CIELAB", which is discussed in *Pocket Guide to Digital Printing* by F. Cost, Delmar Publishers, Albany, N.Y. ISBN 0-8273-7592-1 at pages 144 and 145. This method defines three variables, L*, a*, and b*, which correspond to three characteristics of a perceived color based on the opponent theory of color perception. The three variables have the following meaning:

L*=Lightness (or luminosity), ranging from 0 to 100, where 0=dark and 100=light;

a*=Red/green axis, ranging approximately from −100 to 100; positive values are reddish and negative values are greenish; and b*=Yellow/blue axis, ranging approximately from −100 to 100; positive values are yellowish and negative values are bluish.

Because CIELAB color space is somewhat visually uniform, a single number may be calculated that represents the difference between two colors as perceived by a human. This difference is termed ΔE and calculated by taking the square root of the sum of the squares of the three differences (ΔL*, Δa*, and Δb*) between the two colors. In CIELAB color space, each ΔE unit is approximately equal to a "just noticeable" difference between two colors. CIELAB is therefore a good measure for an objective device-independent color specification system that may be used as a reference color space for the purpose of color management and expression of changes in color. Using this test, color intensities (L*, a*, and b*) may thus be measured using, for instance, a handheld spectrophotometer from Minolta Co. Ltd. of Osaka, Japan (Model # CM2600d). This instrument utilizes the D/8 geometry conforming to CIE No. 15, ISO 7724/1, ASTME1164 and JIS Z8722-1982 (diffused illumination/8-degree viewing system. The D65 light reflected by the specimen surface at an angle of 8 degrees to the normal of the surface is received by the specimen-measuring optical system. Still another suitable optical reader is the reflectance spectrophotometer described in U.S. Patent App. Pub. No. 2003/0119202 to Kaylor, et al., which is incorporated herein in its entirety by reference thereto for all purposes. Likewise, transmission-mode detection systems may also be used in the present invention.

Figure 5:
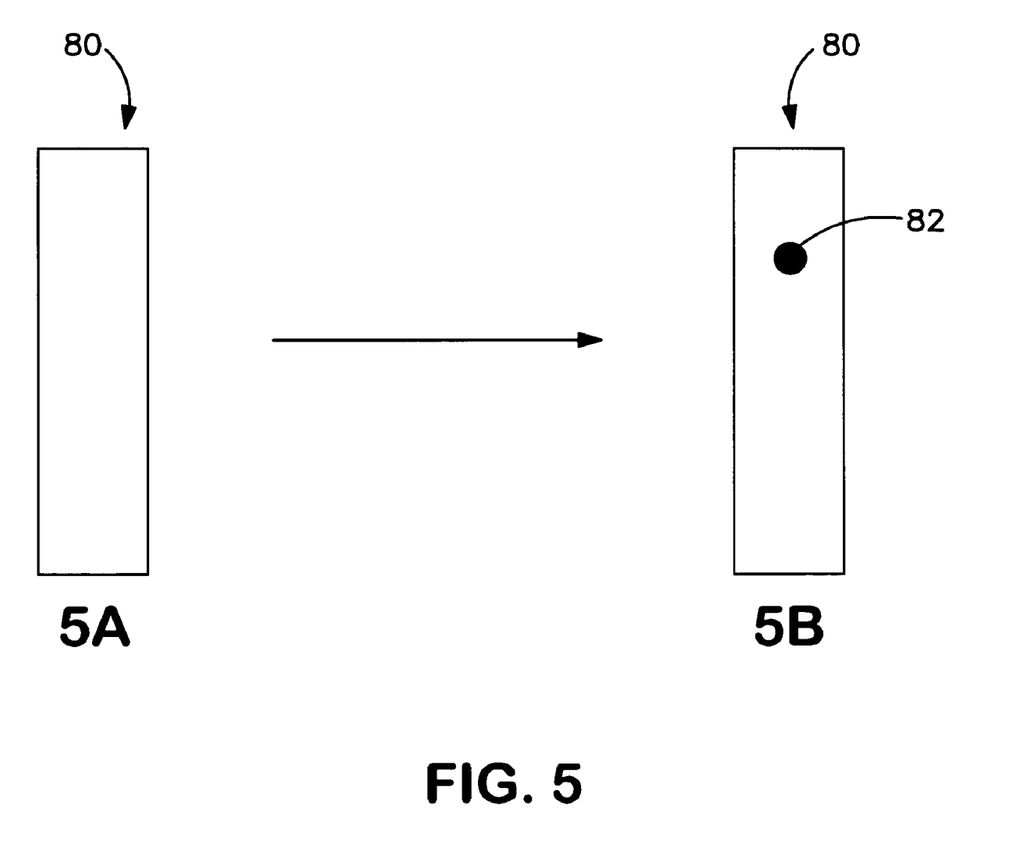
FIG. 5 is a perspective view of a substrate before (FIG. 5A) and after (FIG. 5B) undergoing a color change.

The above-described techniques may be implemented in a variety of ways in accordance with the present invention. For example, a substrate may be utilized that contains a detection zone that provides any number of distinct detection regions (e.g., lines, dots, etc.) so that a user may better determine the presence of one or more microbes within a test sample. Each region may contain the same test chromogen, or may contain different chromogens for reacting with different types of microbes. Some chromogens, for example, are more sensitive to gram-positive bacteria and some are more sensitive to gram-negative bacteria. The test chromogen concentration may also be selectively controlled to provide the desired level of detection sensitivity. For example, higher concentrations may provide a higher level of detection sensitivity when low microbe levels are suspected. Referring to FIG. 5A, one embodiment of the present invention is shown in which a substrate 80 is in the form of a test strip that is uniformly coated with a chromogen (not shown). When an infected ocular test sample (e.g., obtained from a swab) contacts a region 82 of the substrate 80, it changes color to indicate the presence of infection (FIG. 5B).

If desired, the substrate may also contain a control zone that is applied with a control chromogen that is the same or similar to the test chromogen. The control zone does not generally change color during testing so that it may be used for comparison. Similar to the detection zone, the control zone may also provide any number of distinct regions. For example, the control zone may contain regions corresponding to different predetermined microbe concentrations, such as described above. In addition, the regions may contain dyes that have a different sensitivity level for different types of microbes.

Figure 4:
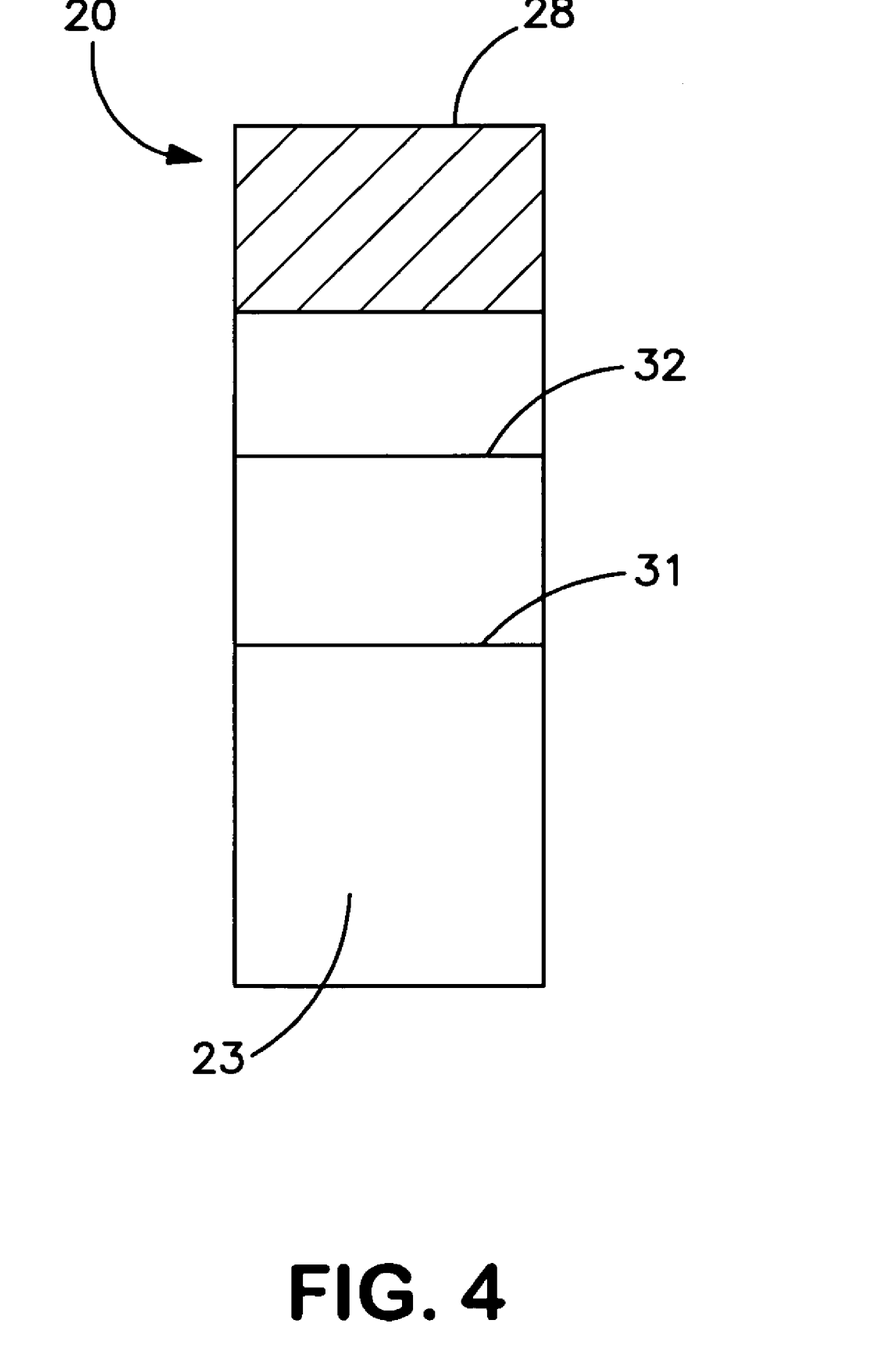
FIG. 4 is a perspective view of a lateral flow assay device that may be used in one embodiment of the present invention.

Referring to FIG. 4, another embodiment of the present invention is illustrated in which the substrate is a lateral flow device 20. More specifically, the device 20 contains a porous membrane 23 that acts as a fluidic medium and is optionally supported by a rigid material (not shown). In general, the porous membrane 23 may be made from any of a variety of materials through which the test sample is capable of passing. For example, the materials used to form the porous membrane 23 may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the porous membrane 23 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms. The device 20 may also contain an absorbent pad 28. The absorbent pad 28 generally receives fluid that has migrated through the entire porous membrane 23. As is well known in the art, the absorbent pad 28 may assist in promoting capillary action and fluid flow through the membrane 23.

To initiate the detection of microbes within a test sample, a user may directly apply the test sample to a portion of the porous membrane 23 through which it may then travel. Alternatively, the test sample may first be applied to a sampling pad (not shown) and/or conjugate pad (not shown) that are in fluid communication with the porous membrane 23. Some suitable materials that may be used to form the sampling pad and conjugate pad include, but are not limited to, nitrocellulose, cellulose, porous polyethylene pads, and glass fiber filter paper. Regardless of where it is applied, the test sample migrates to a detection zone 31 defined by the porous membrane 23 that is capable of signaling the presence of a microbe. In particular, as shown in FIG. 4, the detection zone 31 includes a test dye that exhibits a detectable color change upon contacting one or more microbes. The assay device 20 also employs a control zone 32 that is applied with a control dye and optionally positioned downstream from the detection zone 31. The control zone 20 does not generally change color during testing so that it may be used for semi-quantitative and/or quantitative comparison.

The test and control chromogens are sometimes applied in a manner so that they do not substantially diffuse through the matrix of the porous membrane 23. This enables a user to readily detect the color of the dyes after the desired reaction time. For instance, the chromogens may form an ionic and/or covalent bond with functional groups present on the surface of the porous membrane 23 so that they remain immobilized thereon. In one embodiment, a positively-charged dye may form an ionic bond with negatively-charged carboxyl groups present on the surface of some porous membranes (e.g., nitrocellulose). Alternatively, certain components may be added to a chromogen solution that substantially inhibit the diffusion of the chromogen into the matrix of the porous membrane 23. In other cases, immobilization may not be required, and the chromogen may instead diffuse into the matrix of the porous membrane 23 for reaction with the test sample.

As a result of the present invention, it has been discovered that bacterial infection may be readily detected through the use of a chromogen that undergoes a change in color in the presence of bacteria at a threshold pathogenic concentration. The color change is rapid and may be detected within a relatively short period of time. For example, the chromogen may undergo a detectable color change in less than about 30 minutes, in some embodiments less than about 10 minutes, in some embodiments less than about 5 minutes, in some embodiments less than about 3 minutes, in some embodiments less than about 1 minute, and in some embodiments, less than about 30 seconds. In this manner, the chromogen may provide a "real-time" indication of the presence or absence of bacterial conjunctivitis.

The present invention may be better understood with reference to the following examples.

EXAMPLES

Materials Employed

All reagents and solvents used in the Examples were obtained from Sigma-Aldrich Chemical Co., Inc. of St. Louis, Mo. unless otherwise noted and were used without further purification. All viruses were obtained from Gibraltar Laboratories, Inc. of Fairfield, N.J. Reichardt's dye was also obtained from Sigma-Aldrich Chemical Co, Inc.

Example 1

Figure 1:
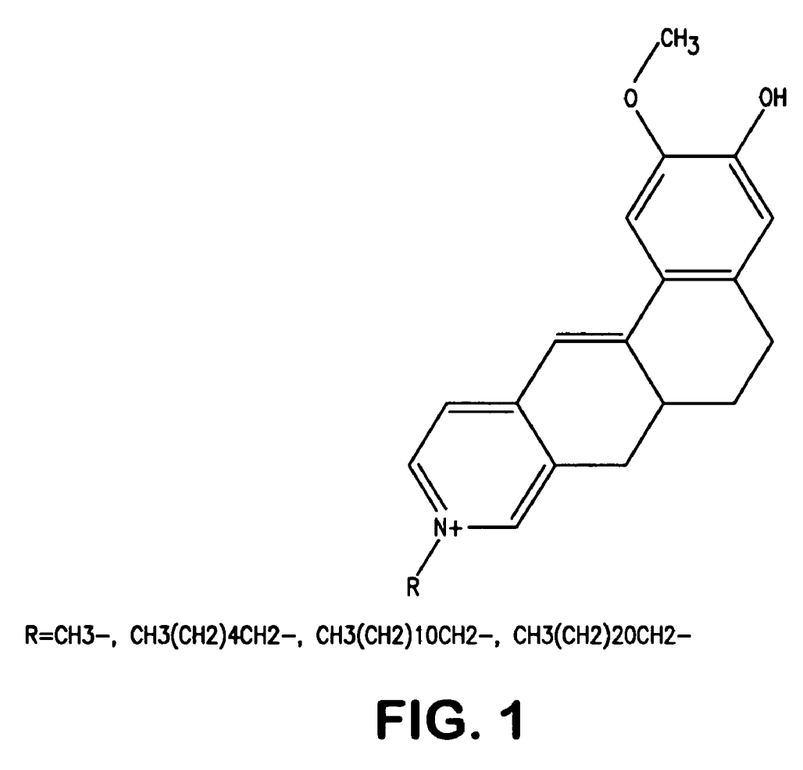
FIG. 1 is the structure of one merocyanine dye that may be used in the present invention.
Figure 2:
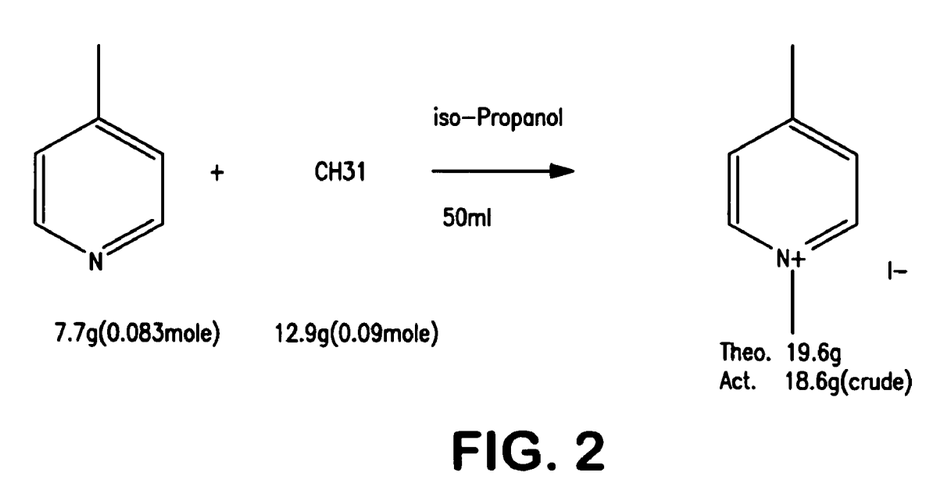
FIGS. 2-3 illustrate one method for synthesizing a merocyanine dye.
Figure 3:
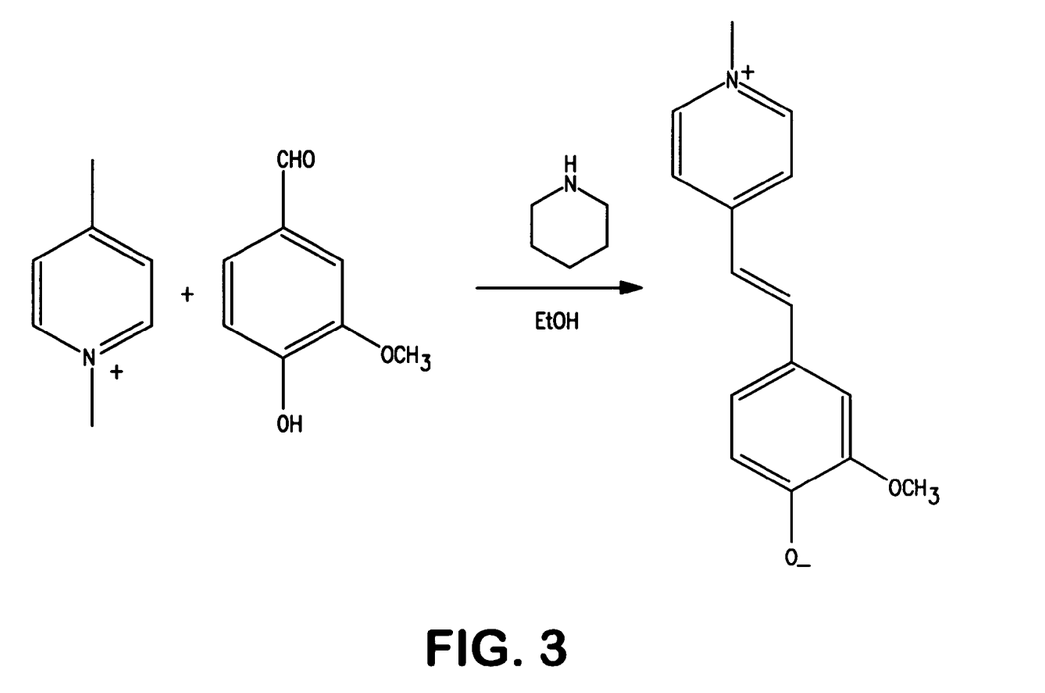

The ability to form merocyanine dyes for use in the present invention was demonstrated. For example, the merocyanine dye shown in FIG. 1 was synthesized in the laboratory using a two-step reaction. Specifically, as shown in FIG. 2, methyl iodide was added slowly to a stirred solution of δ-picoline in 50 milliliters of isopropanol in an ice bath. After addition was complete, the reaction was heated to reflux and reflux continued for 2 hours. The solution was then chilled in an ice-bath and the precipitate filtered, and washed with chilled alcohol, on a Buchner funnel. The powder was then dried in the fumehood for 2 hours. Yield of crude product was 18.6 grams. The crude product was not further purified and used directly for the next step. N-methyl-δ-Picolone (9.4 grams, 0.04 moles), and vanillin (6.1 grams, 0.04 moles) were all dissolved into 50 milliliters of ethanol with stirring as shown in FIG. 3. To this solution was added piperidine (3.4 grams, 0.04 mole) and the mixture refluxed for 16 hours. The reaction mixture was then chilled in an ice-bath and the product filtered off using a Buchner funnel and washed with chilled ethanol. The crude dye of structure 13 was obtained, where R is methyl. The dye was then stirred in 250 milliliters of 0.2 Molar potassium hydroxide solution for 60 minutes to form the zwitterion and then filtered off using a Buchner funnel. The dye was then crystallized from the minimum quantity of a 1:1 water/methanol mixture. The yield was 9.4 grams (98%).

Other merocyanine dyes were also synthesized in a similar manner by selecting an alkyl group of the alkyl iodide to correspond with the desired respective "R" group for the dye. The following Table 1 shows the compounds and the yields obtained for dye structure 13 for three different R groups.

TABLE 1

Alkyl Derivatives Synthesized and the Yields Obtained

| "R" Group | Yield (%) |
|---|---|
| Methyl | 98 |
| Hexyl | 92 |
| Dodecyl | 87 |

Example 2

Adenovirus type 2 pool (ATCC No. VR-846) was propagated in Vero monkey kidney cells and fed with Dulbecco's Modified Eagle's Medium (DMEM), supplemented with fetal calf serum to a concentration of 5% and incubated at 37° C.±1° C. in its presence of 5% $CO_2$ for 6 days. Viral propagation was detected by microscopic observation of infected cell sheets for cellular disintegration (cytopathic effect, CPE) such as rounding, crenation, lysis, pyknosis, etc. as observed in at least 50% of the cell sheet. Cytotoxicity was measured as the extent of cellular disintegration as produced by the agent alone without the virus. Virus was titrated using ten-fold serial dilutions in DMEM, 4 replicates MA 104 cultures per dilution, each replicate inoculated with 0.1 milliliter of virus dilution. The extent of viral replication was calculated as the tissue culture infectious dose-50% (TCID 50) as determined by the method of Reed and Muench. The virus titer was calculated to be $10^{-6.5}$.

*Haemophilus influenzae* (ATCC No. 8149) and *Streptococcus pneumoniae* (ATCC No. 33400) were grown on Chocolate Agar and fed with Trypticase Soy Bean Broth (TSB). *Streptococcus pyogenes* (ATCC No. 49399) was grown on 5% sheep red blood agar and also fed with TSB media. The concentration of these bacteria (in TSB) was found to be $10^8$ CFU/ml. Dilutions of the bacteria ($10^7$, $10^6$ CFU/ml) were created by serially diluted using saline.

Labels were dip-coated with Reichardt's dye (80 milligrams per 10 milliliters in acetonitrile) and allowed to dry to yield a finished product of indicator-coated stickers. 50 microliters of undiluted virus in media was dropped onto a label and allowed to stand for 3 minutes before removing the droplet with a cotton swab. An aliquot of media alone was used as a control. The resulting de-colorization from the Adenovirus droplet was faint and barely above the de-colorization observed for the control media. Aliquots (50 microliters) of $10^7$ and $10^6$ CFU/mL bacteria were also dropped onto stickers, along with drops of the saline control. Drops of $10^8$ CFU/ml bacteria were also dropped onto the stickers, but TSB was used as the control media for these samples. *Haemophilus influenzae* and *Streptococcus pyogenes* exhibited de-colorization above media controls for all CFU/mL levels tested. The de-colorization observed for *Streptococcus pneumoniae* only registered above the control for the $10^8$ CFU/ml concentration. It is of note that the de-colorization observed for all bacteria at the $10^8$ CFU/ml concentration was significantly greater than that observed for the Adenovirus, as was the de-colorization seen for the lesser concentrations of bacteria.

Example 3

A cellulosic towel was used as a substrate onto which *P. aeruginosa* was pipetted onto the towel (100 µl). Reichardt's dye solution (160 mg in 10 ml of acetonitrile) was then added in 10 µl aliquots to the spot and the numbers of drops needed to establish a persistent color were counted. The amount of dye required to maintain a persistent purple color was 80 microliters.

Example 4

A paper-based substrate (Neenah Bond™) (available from Neenah Paper, Inc. of Alpharetta, Ga.) and a label (available from Avery-Dennison) were initially coated with a Reichardt's dye solution (80 milligrams/10 milliliters acetonitrile) and hung to dry. An indicator strip coated with Reichardt's dye was exposed with decreasing amounts of *P. aeruginosa* aliquots. A hand-held spectrophotometer was used to after application of each aliquot to determine "Delta E" value (calculated using L*, A*, and B* values) for each CFU/mL concentration. The results are set forth below in Table 3 (for paper) and Table 4 (for label).

TABLE 3

Results for Paper Substrates

| log CFU/ml | Delta E (*P. aeruginosa*) |
|---|---|
| 8 | — |
| 7 | 4.9569 |
| 6 | 1.3193 |
| 5 | 1.7151 |
| 4 | 2.2358 |
| 3 | 1.7900 |

TABLE 4

Results for Label Substrates

| log CFU/ml | Delta E (*P. aeruginosa*) |
|---|---|
| 7 | 6.9567 |
| 6 | 4.2419 |
| 5 | 4.6519 |
| 4 | 4.9473 |
| 3 | 3.8787 |

Figure 6:
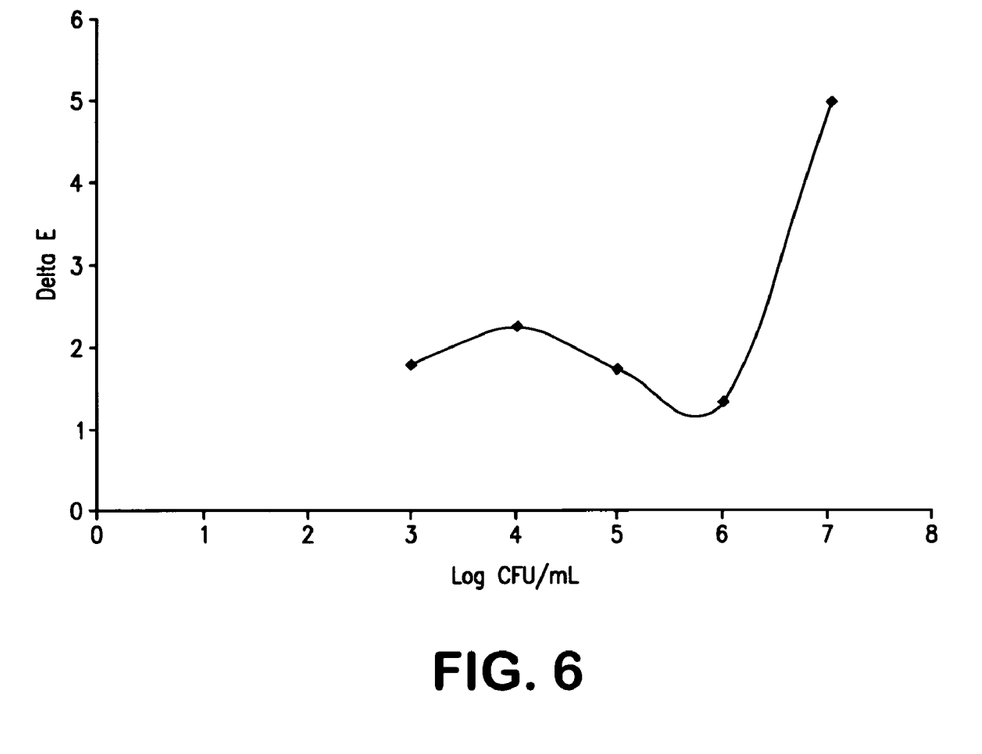
FIG. 6 is a graphical illustration of the results obtained in Example 4 in which Delta E is plotted versus known concentrations of *P. aeuruginosa*.

From the above, standard detection curves were generated as shown in FIG. 6 for *P. aeruginosa*. Thereafter, drops of unknown bacteria concentrations were placed on the stickers and a spectrophotometer was used to measure the "Delta E" of the resulting color. The numerical values obtained for each unknown sample set forth below in Tables 5-6.

TABLE 5

Results for Paper Substrates
*P. aeruginosa*

| log CFU/ml (actual) | Delta E | log CFU/ml (estimated) |
|---|---|---|
| 3 | 1.0267 | 5 |

TABLE 6

Results for Label Substrates
*P. aeruginosa*

| log CFU/ml (actual) | Delta E | log CFU/ml (estimated) |
|---|---|---|
| 6 | 4.4954 | 5 to 6 |
| 6 | 4.1002 | 3 to 6 |

As can be seen from the numerical data, the unknown concentrations were predicted by determining to which known Delta E value the Delta E value of the unknown was closest. Although a few of the results were not completely accurate, the present inventors believe that improving the uniformity of the coating would further enhance detection accuracy.

Example 5

Herpes Simplex Virus 1 (HSV-1) was prepared and inoculated into MA-104 embryonic monkey kidney cells propagated and fed with Dulbecco's Modified Eagle's Medium (DMEM), supplemented with fetal calf serum to a concentration of 5% and incubated at 37° C.±1° C. in its presence of 5% $CO_2$ for 6 days. Viral propagation was detected by microscopic observation of infected cell sheets for cellular disintegration (cytopathic effect, CPE), such as rounding, crenation, lysis, pyknosis, etc., as observed in at least 50% of the cell sheet. Cytotoxicity was measured as the extent of cellular disintegration as produced by the agent alone without the virus. Virus was titrated using ten-fold serial dilutions in DMEM, 4 replicates MA 104 cultures per dilution, each replicate inoculated with 0.1 milliliters of virus dilution. The extent of viral replication was calculated as the tissue culture infectious dose-50% (TCID 50) as determined by the method of Reed and Muench. Reichardt's dye-coated stickers (160 milligrams/10 milliliters acetonitrile, 80 milligrams/10 milliliters acetonitrile, 40 milligrams/10 milliliters acetonitrile, and 20 milligrams/10 milliliters acetonitrile) were used as a test surface. 50 microliters of undiluted virus ($TCID_{50}$ $10^{-7}$ HSV-1/mL) in media was dropped onto each sticker and allowed to stand for 3 minutes before removing the droplet with a cotton swab. The subsequent de-colorization observed was compared to that observed for a virus-free control media and also to a *Salmonella* ($10^8$ CFU/mL) positive control. Though the de-colorization was not as strong as that observed for *Salmonella* bacteria, exposure to undiluted HSV-1 virus led to some de-colorization of the sticker.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for screening for bacterial conjunctivitis, the method comprising contacting an ocular test sample with an N-phenolate betaine dye, wherein the dye undergoes a visible color change in less than about 30 minutes in the presence of bacteria at a pathogenic concentration, and thereafter detecting bacterial conjunctivitis based on the color change.

2. The method of claim 1, wherein the N-phenolate betaine dye has the following general structure:

wherein $R_1$-$R_5$ are independently selected from the group consisting of hydrogen and linear or branched, saturated or unsaturated, substituted or unsubstituted $C_1$ to $C_{20}$ alkyl groups.

3. The method of claim 1, wherein the dye is 4-(2,4,6-triphenylpyridinium -1-yl)-2,6-diphenylphenolate (Reichardt's dye).

4. The method of claim 1, wherein the color change occurs in less than about 10 minutes.

5. The method of claim 1, wherein the color change occurs in less than about 5 minutes.

6. The method of claim 1, wherein the bacteria include *Streptococcus pneumoniae, Haemophilus influenzae, P. aeruginosa, Streptococcus pyogenes*, or combinations thereof.

7. The method of claim 1, wherein the pathogenic concentration is at least about $1 \times 10^5$ colony forming units per milliliter of the ocular test sample.

8. The method of claim 1, wherein the dye is disposed on a substrate.

9. The method of claim 1, wherein the color change occurs in less than about 1 minute.

10. The method of claim 1, wherein the absence of color indicates the presence of bacteria within the ocular test sample at or above the pathogenic concentration.

11. The method of claim 1, wherein the color of the dye is visually detected.

12. The method of claim 1, wherein the color of the dye is quantitatively detected.

13. The method of claim 1, wherein the color of the dye is compared to the color of a control chromogen.

14. The method of claim 1, further comprising differentiating between the presence of a bacterial or viral infection based on the degree that the dye undergoes a color change.

* * * * *